United States Patent [19]

Franzone

[11] 4,285,962
[45] Aug. 25, 1981

[54] PHARMACEUTICAL COMPOSITIONS HAVING ANTI-ULCER ACTIVITY

[75] Inventor: Josè S. Franzone, Turin, Italy

[73] Assignee: Istituto Biologico Chemioterapico "ABC" S.p.A., Turin, Italy

[21] Appl. No.: 180,920

[22] Filed: Aug. 25, 1980

[30] Foreign Application Priority Data

Sep. 26, 1979 [IT] Italy ................................ 26016 A/79

[51] Int. Cl.³ .................... A61K 31/40; A61K 31/405
[52] U.S. Cl. .................................................... 424/274
[58] Field of Search .................................. 424/45, 274

[56] References Cited

U.S. PATENT DOCUMENTS 3,624,103 11/1971 De Martiis .......................... 424/274

OTHER PUBLICATIONS

*Handbook of Nonprescription Drugs,* Fifth Ed., 1977, p. 129, Amer. Pharm. Assoc., Wash. D.C.

*Primary Examiner*—Frederick E. Waddell
*Attorney, Agent, or Firm*—Bucknam and Archer

[57] ABSTRACT

Pharmaceutical compositions are described which exhibit anti-ulcer activity. They contain as the active ingredient an effective amount of 5-methoxy-2-methyl-3-indolylacetohydroxamic acid of formula I

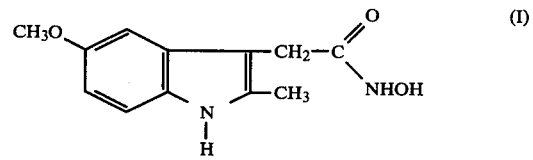

The compositions are suitable for oral administration. The compositions are particularly useful for treatment of ulcers caused by other pharmaceuticals such as pharmaceuticals of the steroid type, but not limited to pharmaceuticals of the steroid type.

4 Claims, No Drawings

PHARMACEUTICAL COMPOSITIONS HAVING ANTI-ULCER ACTIVITY

The present invention relates to pharmaceutical compositions having anti-ulcer activity. More specifically, the present invention relates to compositions having as the active substance 5-methoxy-2-methyl-3-indolylacetohydroxamic acid of formula

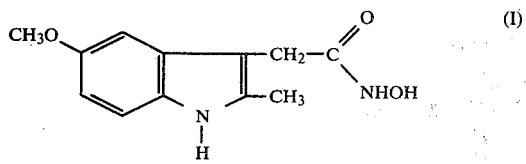

The compound of formula 1 is already known and is described and claimed in U.S. Pat. No. 3,624,103 issued on Nov. 30, 1971. Italian patent application No. 70,092 A/76 filed Dec. 24, 1976, describes another method of preparation of the same substance which may be used in the alternative, in addition to the method of preparation described in the above-mentioned United States patent.

U.S. Pat. No. 3,624,103 describes the anti-inflammatory activity, analgesic and anti-pyretic of the compound of formula I in comparison with other acetohydroxamic acids and indomethacin.

It has now been found surprisingly, that the compound of formula I exhibits a high anti-ulcer activity which permits the use of the substance in the treatment of gastric conditions and peptic ulcers and particularly, ulcers caused by pharmaceuticals such as pharmaceuticals of the cortisone type and other anti-inflammatory substances other than substances of the steroid type. These new therapeutic properties of the compound of formula I are very surprising because the anti-ulcer activity manifests itself at a dose which is very inferior, specifically 5–10 times lower than the dose which is significant in producing anti-inflammatory effects.

It should also be noted that the anti-ulcer activity of the 5-methoxy-2-methyl-3-indolyl-acetohydroxamic acid manifests itself at very low dosages, about 1 mg/kg of body weight; as it will be discussed hereinbelow, this permits to achieve results with the compounds of formula I which are at least the same and frequently superior to the results obtained with very well-known pharmaceuticals used as comparison such as sulpiride, gefarnate and cimetidine which are used in dosages 5–10 times greater.

In addition, the very low toxicity makes the therapeutic index of the substance of formula I extremely favorable.

The invention also relates to the use of the substance I in the therapy of gastric conditions and peptic ulcers and in particular, ulcers caused by pharmaceuticals, such as pharmaceuticals of the cortisone type and anti-inflammatory substances which are not of the steroid type. The invention also relates to the method for the preparation of the substance, the purification and the formulation in a form suitable for the administration and/or the formulation of the substance in containers suitable for the administration.

The substance, 5-methoxy-2-methyl-3-indolylacetohydroxamic acid, is a crystalline substance, white, odorless with a melting point 168°–170° C. The substance is almost insoluble in water in aqueous acidic solutions or basic solutions; almost insoluble in ethanol, diethyl ether and benzene. The substance is sparingly soluble in acetone and propyleneglycol and soluble in dimethylformamide. It may be prepared as mentioned hereinabove according to the process of U.S. Pat. No. 3,624,103 and the process of Italian application No. 70,092 A/76.

The toxicological and pharmacological characteristics of the substance are described hereinbelow. For brevity, the substance is referred to by means of the symbol ABC 8/5.

ACUTE TOXICITY IN RATS BY THE ORAL ROUTE

A suspension of ABC 8/5 in 0.5% carboxymethylcellulose is administered in the amount of 1 ml/100 grams of body weight to Sprague-Dawley male rats of weight 100–150 grams. The animals had been kept fasting for at least 12 hours prior to the treatment. The results are tabulated hereinbelow in Table 1. As shown by the data, the very low toxicity of ABC 8/5 has not been permitted to establish the $LD_{50}$ by the oral route.

TABLE 1

| Dosage mg/kg | Number of Animals Treated | Animals Dead | Mortality % |
|---|---|---|---|
| 40 | 10 | 0/10 | 0 |
| 80 | 10 | 0/10 | 0 |
| 120 | 10 | 0/10 | 0 |
| 200 | 10 | 0/10 | 0 |
| 320 | 10 | 0/10 | 0 |
| 520 | 10 | 0/10 | 0 |
| 840 | 10 | 0/10 | 0 |
| 1360 | 10 | 0/10 | 0 |
| 2200 | 10 | 0/10 | 0 |
| 3560 | 10 | 0/10 | 0 |
| 5760 | 10 | 0/10 | 0 |

ACUTE TOXICITY IN RATS BY THE INTRAPERITONAL ROUTE

A suspension of the compound in 0.5% carboxymethylcellulose is administered in the amount of 1 ml/100 grams of body weight by the intraperitonal route to Sprague-Dawley rats of 100–150 grams weight. Also, in this case, the animals had been kept fasting for a period of at least 12 hours prior to the treatment. The results are shown hereinbelow in Table 2. The $LD_{50}$ by the intraperitonal route is 980 ml/kg determined by the method of preparation.

The mortality is determined on the seventh day after administration.

TABLE 2

| Dosage mg/kg | No. of Animals Treated | Animals Dead | Mortality % |
|---|---|---|---|
| 40 | 10 | 0/10 | 0 |
| 80 | 9 | 0/10 | 0 |
| 120 | 10 | 1/10 | 10 |
| 200 | 10 | 2/10 | 20 |
| 320 | 10 | 0/10 | 0 |
| 520 | 10 | 4/10 | 40 |
| 840 | 10 | 4/10 | 40 |
| 1360 | 10 | 6/10 | 60 |
| 2200 | 10 | 10/10 | 100 |

CUMULATIVE TOXICITY IN RATS BY THE ORAL ROUTE

There are used Sprague-Dawley male rats of 200–250 grams by weight. The substance ABC 8/5 is suspended in 0.5% carboxymethylcellulose and is administered to the animals in the amount of 1 ml/100 grams of body weight. The rats are treated daily with increasing dosages of the compound. The results are tabulated in Table 3 hereinbelow. The results show that the cumulative toxicity is so low that the $LD_{50}$ cannot be determined.

TABLE 3

| Oral Dosage mg/kg | No. of animals | Mortality | Mortality Percent |
| --- | --- | --- | --- |
| 840 | 50 | 0/50 | 0 |
| 1360 | 50 | 0/50 | 0 |
| 2200 | 50 | 0/50 | 0 |
| 3560 | 49 | 1/50 | 2 |
| 5760 | 45 | 4/49 | 8.16 |

CUMULATIVE TOXICITY IN RATS BY THE INTRAPERITONAL ROUTE

The substance ABC 8/5 suspended in 0.5% carboxymethylcellulose is administered to Sprague-Dawley male rats of 200-250 grams weight in the amount of 1 ml/100 grams of body weight. The animals are treated daily with increasing dosages of the compound. The results are tabulated hereinbelow in Table 4. The cumulative $LD_{50}$ by the intraperitonal route is equal to 1050 ml/kg.

TABLE 4

| Intraperitonal Dosage mg/kg | No. of animals | Mortality | Mortality Percent |
| --- | --- | --- | --- |
| 80 | 50 | 0/50 | 0 |
| 120 | 50 | 0/50 | 0 |
| 200 | 50 | 0/50 | 0 |
| 320 | 49 | 1/50 | 2 |
| 520 | 47 | 2/49 | 4.08 |
| 840 | 34 | 13/47 | 27.65 |
| 1360 | 8 | 26/34 | 76.47 |
| 2200 | 0 | 8/8 | 100 |

ANTI-ULCER ACTIVITY IN RATS (a) Ulcers resulting from pinching the pylorus

The method of Shay with Sprague-Dawley female rats of 140-180 grams weight is used. The rats are kept fasting for a period of 48 hours prior to the operation and afterwards the animals are treated with ABC 8/5 and with the pharmaceuticals used by way of comparison suspended in 0.5% carboxymethylcellulose, the substances being administered by the intraperitonal route at the rate of 1 ml/100 grams of body weight. Four hours after the administration, the animals are killed and the extent of gastric ulcers is determined according to the following criterion.

0 = No ulcer or lesion
1 = Hemorrhagic areas, but less than 5 microulcerations
2 = More than 5 microulcerations or a more extended ulceration
3 = More than 1 extended ulceration or perforations The results are reported hereinbelow in Table 5 which shows that the pinching of the pylorus is followed by the formation of gastric ulcers in the rats used as a control with an average ulcerogenic index of 2.92. To state the matter in different words, all the animals show more than one visible ulcer or one perforation according to the criterion indicated hereinabove. Increasing dosages of ABC 8/5 are followed by a significant decrease of the ulcerogenic index with a maximum decrease of −48.63% for a dose of 1 ml/kg of body weight. A further increase in the dosage does not cause any correlation between the dosage and the results achieved. It should be stressed that in this test, ABC 8/5 is much more active than gefarnate or sulpiride and at least equally active as cimetidine.

TABLE 5

| Treatments | No. of animals | Average ulcerogenic index ± SD | % of inhibition with respect to the control animals |
| --- | --- | --- | --- |
| Control Animals | 19 | 2.92 ± 1.97 | — |
| 8/5 i.p. | | | |
| 0.50 mg/kg | 19 | 1.92 ± 1.70 | −34.24% |
| 1 mg/kg | 19 | 1.50 ± 1.09 | −48.63% |
| 10 mg/kg | 7 | 2.00 ± 0.58 | −31.51% |
| Cimetidine i.p. | | | |
| 1 mg/kg | 12 | 1.71 ± 0.49 | −41.44% |
| 10 mg/kg | 7 | 2.71 ± 2.14 | −7.19% |
| Sulpiride i.p. | | | |
| 10 mg/kg | 20 | 2.15 ± 1.67 | −26.36% |
| Gefarnate i.p. | | | |
| 10 mg/kg | 17 | 2.25 ± 1.81 | −22.94% |
| 40 mg/kg | 14 | 2.57 ± 1.15 | −11.99% |

(b) Ulcers caused by prednisolone

Wistar rats of 150-200 grams are treated subcutaneously for three days with prednisolone in the amount of 8 mg/rat/day, the substance being suspended in 0.2 ml of olive oil and orally with ABC 8/5 or gefarante or sulpiride in the following dosages.

| -ABC 8/5 | 0.5-1-10-20 | mg/kg orally, in CMC |
| --- | --- | --- |
| -Gefarnate | 10-20 | mg/kg orally, in CMC |
| -Sulpiride | 10-20 | mg/kg orally, in CMC |

The animals are kept fasting since the first day of treatment. The ulcerations are determined according to the following criterion.

0 = no ulcerations or lesions
1 = hemorrhagic areas
2 = less than 5 microulcerations
3 = more than 5 microulcerations or a more extended ulceration
4 = more than one extended ulceration
5 = perforations The results are tabulated in Table 6 hereinbelow. It should be noted that treatment with prednisolone causes in the control rats gastric ulcers with an average ulcerogenic index of 3.83. The oral administration simultaneously of increasing doses of ABC 8/5 for a period of three days, prevents to a great extent in all the animals the ulcerogenic activity of prednisolone as shown by the fact that the ulcerogenic index is reduced up to a maximum of 81.4% with a dose of 1 ml/kg of body weight. It should be stressed that with every dosage of ABC 8/5, the inhibition achieved is greater than 50%.

In this test, gefarnate is very active and also sulpiride is substantially active. However, gefarnate reaches the maximum effect at a dose which is ten times the dose of ABC 8/5 and sulpiride reaches the maximum effect, but always less than the effect of ABC 8/5 at a dose which is 20 times greater.

TABLE 6

| Treatment | No. of animals treated | No. of animals dead | Average ulcerogenic Index ± SD | % of inhibition with respect to control animals |
| --- | --- | --- | --- | --- |
| Control | | | | |

TABLE 6-continued

| Treatment | No. of animals treated | No. of animals dead | Average ulcerogenic Index ± SD | % of inhibition with respect to control animals |
|---|---|---|---|---|
| Animal 8/5 orally | 7 | 0 | 3.83 ± 1.47 | — |
| 0.50 mg/kg | 7 | 0 | 1.83 ± 0.75 | −53.0% |
| 1 mg/kg | 7 | 0 | 0.71 ± 1.49 | −81.4% |
| 10 mg/kg | 7 | 0 | 1.42 ± 1.90 | −62.8% |
| 20 mg/kg Gefarnate orally | 7 | 0 | 1.14 ± 2.03 | −70.2% |
| 10 mg/kg | 7 | 1 | 0.33 ± 0.82 | −91.4% |
| 20 mg/kg Sulpiride orally | 7 | 0 | 1.14 ± 1.07 | −70.2% |
| 10 mg/kg | 7 | 0 | 1.71 ± 1.49 | −55.3% |
| 20 mg/kg | 7 | 0 | 1.57 ± 2.15 | −59.0% |

(c) Ulcers caused by phenylbutazone

Wistar male rats of average weight 230–400 grams are treated orally with the following substances suspended in 0.5% CMC.

| -ABC 8/5 | 0.5-1-5 mg/kg | in the |
|---|---|---|
| -Gefarnate | 10-20 mg/kg | amount of 1 ml/100 grams |
| -Sulpiride | 10-20 mg/kg | body weight |

Thirty minutes after the oral treatment, 100 ml/kg of phenylbutazone in the amount of 1 ml/100 grams of body weight are administered intraperitonally. Six hours after this administration all the animals are killed.

The ulcerations are estimated according to the criterion illustrated hereinabove under (b). The results are tabulated in Table 7 hereinbelow. The results show that the treatment with phenylbutazone causes in the control animals, gastric ulcers with an average ulcerogenic index of 3.42.

The simultaneous oral administrations of increasing doses of ABC 8/5 prevents in all the animals, the ulcerogenic activity of phenylbutazone: the ulcerogenic index is reduced up to a maximum of 56.68% with a dosage of 0.5 mg/kg. Sulpiride and gefarnate show a protective activity which is substantially inferior to the activity of ABC 8/5 even when they are administered at a much higher dosage.

TABLE 7

| Treatment | No. of animals | Average ulcerogenic index ± SD (SE) | % of inhibition with respect to control animals |
|---|---|---|---|
| Control Animal | 14 | 3.42 ± 1.64 (0.43) | — |
| 8/5 0.5 mg/kg/orally + FNB 100 mg/kg i.p. | 9 | 1.55 ± 1.23 (0.40) | −56.68% |
| 8/5 1 mg/kg/orally + FNB 100 mg/kg/i.p. | 10 | 2.00 ± 1.20 (0.36) | −41.50% |
| 8/5 5 mg/kg/orally + FNB 100 mg/kg/i.p. | 10 | 2.30 ± 1.63 (0.50) | −32.75% |
| Sulpiride 10 mg/kg/orally + FNB 100 mg/kg/i.p. | 10 | 3.20 ± 1.51 (0.48) | −6.43% |
| Sulpiride 20 mg/kg/orally + FNB 100 mg/kg/i.p. | 10 | 2.00 ± 1.15 (0.36) | −41.50% |
| Gefarnate 10 mg/kg/orally + FNB 100 mg/kg/i.p. | 10 | 2.00 ± 1.41 (0.44) | −41.50% |
| Gefarnate 20 mg/kg/orally + FNB 100 mg/kg/i.p. | 10 | 1.80 ± 1.13 (0.34) | −47.37% |

(d) Ulcers caused by low temperatures and immobilization

Wistar male rats of body weight 250–350 grams are kept fasting for a period of 24 hours. All the pharmaceuticals are administered by the oral route in CMC. Immediately after the treatment, the animals are placed in cages and then in a cold room at a temperature of 4° C. for a period of 4 hours. The rats are then killed by decapitation and the gastric ulcers are estimated according to the criterion discussed hereinabove under (b). The results are reported in Table 8 hereinbelow. The data show that in the control animals, the ulcerogenic index is 1.86. The simultaneous oral administration of ABC 8/5 with increasing doses is followed by a maximum inhibition of the ulcerogenic index corresponding to a dose of 2.5 mg/kg (−42.5%). In this test, the antiulcerogenic activity of ABC 8/5 is substantially superior to the activity of both gefarnate and cimetidine while it is comparable to the activity of sulpiride. However, the activity of sulpiride reaches the maximum effect at a dosage which is eight times higher.

TABLE 8

| Treatment | No. of animals | Average ulcerogenic index ± SD | % of inhibition with respect to control animals |
|---|---|---|---|
| Control animals CMC 0.5% orally | 43 | 1.86 ± 1.24 | — |
| 8/5 orally | | | |
| 0.50 mg/kg | 21 | 1.57 ± 1.36 | −15.59% |
| 1 mg/kg | 21 | 1.43 ± 1.16 | −23.12% |
| 2.5 mg/kg | 14 | 1.07 ± 1.21 | −42.50% |
| 5 mg/kg | 21 | 1.52 ± 1.33 | −18.28% |
| Gefarnate orally | | | |
| 10 mg/kg | 21 | 1.33 ± 1.35 | −28.49% |
| 20 mg/kg | 21 | 1.57 ± 1.47 | −15.59% |
| Sulpiride orally | | | |
| 10 mg/kg | 21 | 1.24 ± 1.41 | −33.30% |
| 20 mg/kg | 21 | 1.05 ± 1.20 | −43.50% |
| Cimetidine orally | | | |
| 10 mg/kg | 14 | 1.43 ± 1.16 | −23.1% |

PROTECTIVE ACTION OF ABC 8/5 ON THE ACUTE ORAL TOXICITY OF OXAMETHACIN AND INDOMETHACIN IN RATS

It has been found that the simultaneous oral administration of ABC 8/5 in a dose of 1 ml/kg increases the $LD_{50}$ both of indomethacin and oxamethacin (1-(p.chlorobenzoyl)-5-methoxy-2-methyl-3-indolyl-acetohydroxamic acid) and, therefore, decreases the acute toxicity of these substances. As it is shown in Table 9 hereinbelow, the increase of $LD_{50}$ is in the order of 100%.

TABLE 9

| | $LD_{50}$ in rats, mg/kg | |
|---|---|---|
| Treatment | 4th day | 7th day |
| Indomethacin orally | 32.0 | 21.0 |
| Oxamethacin orally | 104.0 | 94.0 |
| Indomethacin orally + ABC 8/5 1 mg/kg orally | 47.0 | 45.0 |
| Oxamethacin orally + ABC 8/5 1 mg/kg orally | 220.0 | 191.0 |

It is obvious that the decrease of toxicity of pharmaceuticals used as anti-inflammatory agents has great value therapeutically and this is particularly so in the case of oxamethacin and indomethacin, due to the contemporaneous administration of 5-methoxy-2-methyl-3- indolyl-acetohydroxamic acid. It should also be noted that all the most important data reported in the preceding tables are statistically significant. Compound I may be administered in a variety of pharmaceutical formulations such as for example:

(1) compresses which contain 25 mg of compound I in addition to the conventional additives and excipients used in conventional operations of pharmaceutical formulations.

(2) capsules of hard gelatin which contain 50 mg of compound I dispersed in conventional excipients.

(3) envelopes which contain an effervescent substance which contains 25 mg of compound I and an excipient capable of producing an effervescent suspension when the content of the envelope is placed in water.

The daily dosage may be as follows:

2–4 compresses containing 25 mg of compound I daily during meals;

1–3 capsules containing 50 mg of compound I daily during meals;

2–4 envelopes containing the material capable of producing effervescence and containing 25 mg of compound I daily during meals.

It is clear, however, that other pharmaceutical formulations may be used and that the formulations listed hereinabove are only given by way of example.

What is claimed is:

1. The method of treatment of gastritis and peptic ulcers in a living patient in need of said treatment which consists of administering to said patient an effective amount of 5-methoxy-2-methyl-3-indolyl-acetohydroxamic acid of formula I

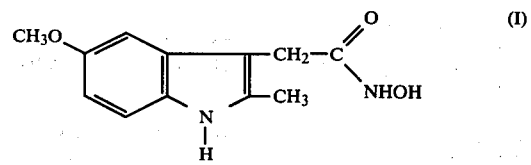

2. The method according to claim 1 wherein said gastritis and peptic ulcers are caused by pharmaceuticals of the steroid type.

3. The method according to claim 1 wherein said gastritis and peptic ulcers are caused by at least one member of the group consisting of prednisolone, phenylbutazone, oxamethacin, and indomethacin.

4. The method according to claim 1 wherein said gastritis and peptic ulcers are caused by low temperatures.

* * * * *